US006451292B2

United States Patent
Warford, III et al.

(10) Patent No.: US 6,451,292 B2
(45) Date of Patent: Sep. 17, 2002

(54) METHODS FOR DENTISTRY USING COMPOSITIONS COMPRISING AN OIL

(75) Inventors: John H. Warford, III, Bismarck, ND (US); Edward C. Combe, Maplewood, MN (US); John H. Warford, II, Bismarck, ND (US)

(73) Assignee: Dakota Dental Development, Inc., Bismark, ND (US)

( * ) Notice: Subject to any disclaimer, the term of this patent is extended or adjusted under 35 U.S.C. 154(b) by 0 days.

(21) Appl. No.: 09/944,822

(22) Filed: Aug. 31, 2001

Related U.S. Application Data

(62) Division of application No. 09/427,876, filed on Oct. 27, 1999, now Pat. No. 6,342,203.

(51) Int. Cl.[7] .................................................. A61K 7/16
(52) U.S. Cl. ...................... 424/49; 433/226; 433/228.1; 106/34
(58) Field of Search .............................. 424/49; 166/35; 433/2, 222.1, 226, 228.1

(56) References Cited

U.S. PATENT DOCUMENTS

| | | | |
|---|---|---|---|
| 3,943,949 A | | 3/1976 | Ashton et al. |
| 4,182,035 A | | 1/1980 | Yamauchi et al. |
| 4,222,780 A | | 9/1980 | Shibatani et al. |
| 4,235,633 A | | 11/1980 | Tomioka et al. |
| 4,259,075 A | | 3/1981 | Yamauchi et al. |
| RE31,954 E | | 7/1985 | Fine et al. |
| 4,773,933 A | | 9/1988 | Futami et al. |
| 4,968,725 A | | 11/1990 | Mukai et al. |
| 5,063,257 A | | 11/1991 | Akahane et al. |
| 5,080,583 A | | 1/1992 | Hunting |
| 5,154,613 A | * | 10/1992 | Cohen ...................... 433/228.1 |
| 5,252,697 A | | 10/1993 | Jacobs et al. |
| 5,522,725 A | | 6/1996 | Jordan et al. |
| 5,554,030 A | | 9/1996 | Ario et al. |
| 5,575,645 A | | 11/1996 | Jacobs et al. |
| 5,595,487 A | | 1/1997 | Ario et al. |
| 5,639,239 A | | 6/1997 | Earle |
| 5,645,429 A | | 7/1997 | Blackwell et al. |
| 5,662,886 A | | 9/1997 | Oxman et al. |
| 5,696,181 A | | 12/1997 | Chang et al. |
| 5,711,665 A | | 1/1998 | Adam et al. |
| 5,756,559 A | | 5/1998 | Blackwell et al. |
| 5,900,230 A | | 5/1999 | Cutler |
| 5,932,627 A | | 8/1999 | Blackwell |
| 5,961,958 A | | 10/1999 | Homola et al. |
| 6,342,203 B2 | * | 1/2002 | Warford, III et al. ......... 424/49 |

FOREIGN PATENT DOCUMENTS

| | | |
|---|---|---|
| EP | 0 674 896 A1 * | 10/1995 |
| GB | 948 204 | 1/1964 |
| WO | WO99/072329 | 2/1999 |

OTHER PUBLICATIONS

Herczegh A. Investigation of the Resistance to Bacteria of Several Photopolymerized Tooth Filling Materials and Glass Ionomer Cement. Dental Review 84(5)151–154, May 1991. English translation of Hungarian article provided.*

O'Brien, "Dental Materials and Their Selection," Appendix A, p. 332, 1997.

Sano et al., "Relationship between surface area for adhesion and tensile bond strength—Evaluation of a micro–tensile bond test," *Dental Materials*, Jul. 1994, pp. 236–240.

\* cited by examiner

*Primary Examiner*—Ralph Gitomer
(74) *Attorney, Agent, or Firm*—Kagan Binder, PLLC

(57) ABSTRACT

The present invention provides a method of utilizing a non-metallic composition to adhere one or more dental or orthodontic fixtures to hard dental tissue, wherein the non-metallic compositions harden in the mouth to form substantially permanent fixtures. The compositions comprise an amount of an essential oil effective to alter the sensory properties, i.e., the taste or smell, of the composition, and that desirably imparts a pleasant taste and/or odor. The essential oil further advantageously provides the composition, once hardened in the mouth, with a surface more hydrophobic than a corresponding composition, thereby inhibiting the deposition or formation of bacterial plaque.

26 Claims, No Drawings

METHODS FOR DENTISTRY USING COMPOSITIONS COMPRISING AN OIL

REFERENCE TO RELATED APPLICATION

This is a division of Application No. 09/427,876 filed Oct. 27, 1999 now U.S. Pat. No. 6,342,203.

Reference is hereby made to commonly-assigned application Ser. No. 10/013,441 entitled FLAVORED TOOTH CONDITIONING COMPOSITIONS AND METHODS FOR USING THE COMPOSITIONS TO CONDITION A TOOTH SURFACE filed on even date herewith.

FIELD OF THE INVENTION

This invention relates to compositions that harden in the mouth to repair, restore, adhere to, or protect, the surface of a tooth. In particular, the present invention relates to non-metallic compositions that comprise an amount of an essential oil and that are intended to be substantially permanent once hardened within the mouth. The inclusion of the essential oil can provide many advantageous properties to the compositions, e.g., a more pleasant flavor and/or odor; hydrophobicity, which in turn renders the hardened compositions with a greater plaque resistance; and enhanced processing and handling characteristics. The invention also relates to methods for repairing, restoring, adhering to, or protecting a tooth by using the compositions as sealants, restoratives, composites and adhesives.

BACKGROUND OF THE INVENTION

Adhesion procedures are utilized in many forms of dental treatment. For example, adhesives are used in orthodontic treatment to adhere metal or ceramic brackets directly to tooth enamel. For the prevention of tooth decay, resin-based materials, called pit and fissure sealants, are often bonded to enamel to provide a coating that protects the enamel from decay. Additionally, adhesives may be used to secure the adhesion of a tooth filling material at its margins with enamel and dentin, in order to reduce or eliminate the penetration of microbial agents across these margins. Adhesive materials may also be used to restore teeth in a number of ways. In particular, when a minor restoration or repair is required, e.g., as when a tooth is missing an incisal edge, new material can be bonded to the surface of the tooth to replace the tooth material that has been lost, rather than removing extensive additional tooth material in order to place a crown. Adhesive materials are also used in situations where a greater amount of oral rehabilitation is required, as in the cementing of inlays, crowns and bridges. Adhesive technology is also used in aesthetic dentistry, where veneers can be cemented on to the enamel facing of teeth to mask defects or areas of discoloration.

It can thus be seen that adhesion procedures are central to the practice of dentistry. Advantageously, in recent years, adhesive materials have been developed that are not only more durable than adhesive materials of years past, but that are also capable of forming substantially permanent bonds with and between the materials to which they bond. Thus, when utilized in their respective applications, these materials are capable of performing their desired function for long periods of time, i.e., years or even a lifetime, thus potentially reducing the frequency of required dental treatment.

Although these materials are widely used in contemporary dental practice, and are generally extremely effective in each of their respective applications, there still exist areas in which improvements to adhesive materials would be desirable, i.e., that would result in the further enhancement or optimization of the properties of these materials. For example, many adhesive materials have a bitter taste, and leave an unpleasant after-taste in the mouth, which may be particularly problematic when the patient being treated is a child. Additionally, some of these materials, when hardened, can attract and/or contribute to the formation of bacterial plaque on the surfaces thereof due to the fact that these surfaces are generally not sufficiently hydrophobic to prevent such plaque accumulation. Finally, some of the aforementioned materials are difficult to handle or to mold into the desired shape and placement in the mouth, lengthening the time required to perform certain procedures utilizing these materials.

It would thus be desirable to provide materials with either no substantial flavor and/or odor, or more preferably, with a pleasant flavor and/or odor. It would further be desirable to provide materials which inhibit the ability of bacterial plaque to form on these materials when hardened in the mouth. Finally, such materials would desirably be easily and conveniently shaped and placed within the mouth, so that the amount of time required to do so is desirably reduced.

SUMMARY OF THE INVENTION

The present invention is drawn to compositions that harden in the mouth to repair, restore, adhere to, or protect, the surface of a tooth. In particular, the present invention relates to non-metallic compositions that comprise an amount of an essential oil and that are intended to be substantially permanent once hardened within the mouth. The inclusion of the essential oil can provide many advantageous properties to the compositions, e.g., a more pleasant flavor and/or odor; hydrophobicity, which in turn renders the compositions when hardened with a greater plaque resistance; and enhanced processing and handling characteristics.

Thus, in one aspect, the present invention provides non-metallic compositions for use in dentistry comprising an essential oil in an amount effective to alter one or more of the sensory properties of the non-metallic composition and wherein the non-metallic composition hardens in the mouth to form a substantially permanent feature within the mouth.

In another aspect, the present invention provides non-metallic composition for use in dentistry comprising an essential oil wherein the non-metallic composition hardens in the mouth to form a substantially permanent feature and wherein the essential oil is present in an amount effective to provide the feature with a substantially hydrophobic surface.

Because the essential oil imparts a more hydrophobic nature to the surface of the non-metallic compositions when hardened, the surface of the hardened compositions are less susceptible to the formation of bacterial plaque. Thus, the compositions of the present invention find particular utility when used in methods to repair or seal a tooth surface. As a result, in another aspect, the present invention provides a method for repairing or sealing hard dental tissue comprising applying to said tissue a non-metallic composition comprising an essential oil; and causing said composition to harden on said tissue. Once hardened, the composition is intended to be a substantially permanent feature on said tissue.

In addition to the advantageous properties afforded to compositions by virtue of the inclusion of the essential oil, the essential oils also advantageously do not substantially interfere with the ability of the inventive compositions to harden and to form substantially permanent bonds with a tooth surface, or between a tooth surface and an additional dental material, e.g., such as a crown or bridge. This is a surprising and unexpected result inasmuch conventional dental knowledge teaches that some oils can interfere with the ability of polymerizing materials to harden or cure, and also that in general, oils interfere with the adhesive bonding of materials to tooth substance.

Thus, in another aspect, the present invention provides a method of adhering a dental or orthodontic fixture to hard dental tissue comprising applying to said tissue a non-metallic composition comprising an essential oil; placing the dental or orthodontic fixture in adhesive contact with the composition; and causing the composition to harden on said tissue to adhere the fixture to the dental tissue in a manner so as to render the fixture a substantially permanent feature on the tissue.

As used herein, the phrase "non-metallic composition" is meant to indicate tooth-colored compositions, i.e., non-amalgam based compositions, useful to repair, restore, adhere to, or protect, the surface of a tooth. Such compositions are typically based upon polymer, compomer or ionomer systems and although the term "non-metallic" is used to further clarify they types of materials contemplated to be useful in the compositions of the present invention, this term is not meant to preclude the compositions from comprising amounts of metals. For example, certain cements derived from glass-ionomers can contain amounts of metals, such as silver, in amounts that although not insignificant, do not interfere or participate in the hardening reaction and that do not result in the hardened materials having a metallic appearance.

Also, as used herein, the phrase "substantially permanent" as it is used pertaining to the bond between the tooth (either enamel or dentin) and an composition according to the present invention, or to the bond provided by the composition between a tooth and another dental material, e.g., a crown, is meant to indicate a bond that is sufficiently strong and secure, so that the composition or applied dental material will be a substantially permanent feature within the mouth, i.e., that at least at the time that the composition and/or dental material is applied, the material is intended to remain adhered to the tooth structure indefinitely. Thus, the phrase "substantially permanent" does not exclude dental materials that, due to extenuating circumstances unrelated to the initial integrity of the bond between the material and the tooth, fail prematurely. Generally speaking, a bond strength of at least about 5 MPa, and preferably from about 15 MPa to about 35 MPa is sufficiently strong so as to render dental materials adhered to tooth structure with this bond strength "substantially permanent." Of course, those of ordinary skill in the art readily recognize that bond strengths indicative of permanence can vary dependent upon the material being bonded, the tooth structure being bonded to, and furthermore, that measured bond strengths are dependent upon the method of testing and the history of the extracted teeth used for the testing. Bond strength may be measured, for example, as described below in connection with Examples 7 and 8. See also, e.g., William J. O'Brien, PhD, "Dental Materials and Their Selection," 2nd ed., p. 332 (1997). It should be noted that higher bond strengths can be obtained using micro-testing methods such as those disclosed in Sano et al., "Relationship between surface area for adhesion and tensile bond strength—Evaluation of a micro-tensile bond test." Dent Mater 10:236, July, 1994.

Additionally, the compositions in accordance with the present invention advantageously include an amount of an essential oil sufficient to alter one or more of the sensory properties, i.e., taste or smell, of the compositions. That is, the essential oil may simply act to ameliorate and otherwise unpleasant taste, or desirably, may impart a more pleasing flavor and/or odor to the composition.

Finally, as used herein, the term "hydrophobic" or "hydrophobicity" as it relates to a surface of a composition in accordance with the present invention once it has hardened within the mouth, is meant to indicate that the surface is more hydrophobic than the surface of a hardened analogous composition that does not comprise an amount of an essential oil. The hydrophobicity, or wettability, of a surface may be measure in a number of ways well known to those of ordinary skill in the art. For example, one method of measuring the hydrophobicity is by use of a dynamic contact angle analyzer, which is described further in connection with Example 9, hereinbelow.

Unless otherwise indicated, as used herein, all references to percentages are percentages by weight of the composition.

DETAILED DESCRIPTION OF THE INVENTION

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

The present invention provides non-metallic compositions for use in dentistry that comprise one or more essential oils. The inclusion of one or more essential oils in the otherwise conventional compositions provides these compositions with many advantageous properties. First of all, the essential oil(s) are capable of either ameliorating the unpleasant flavor, or imparting a pleasant flavor to, conventional compositions that otherwise would have a bitter and potentially unpleasant taste and/or odor. Additionally, the inclusion of an essential oil in conventional compositions is capable of rendering the surface of such compositions, when hardened in the mouth, with a more hydrophobic surface than the same composition would have it not for the inclusion of the oil. The fact that the inclusion of one or more essential oils in conventional compositions provides the aforementioned benefits is extremely advantageous when the inventive compositions are utilized in dental practice.

Furthermore, not only is the inclusion of such oils not otherwise detrimental to the properties of these compositions, i.e., does not substantially interfere with the ability of the composition to harden to form a substantially permanent feature within the mouth, but the essential oils may actually improve the handleability of these compositions. That is, while many compositions are difficult to shape or place in the mouth in some circumstances due to their putty-like consistency, the compositions in accordance with the present invention are provided with a more fluid consistency, which renders them easier to place.

The inclusion of oils in these types of compositions to provide the aforementioned benefits has not previously been considered a viable option to provide such benefits due to the fact that oils have previously been thought to interfere with the ability of the compositions to form substantially permanent bonds to a tooth surface or with an additional dental material. However, it has now been surprisingly discovered that the oils suitable for use in the present invention can be easily and conveniently incorporated into conventional non-metallic compositions to provide these benefits, without concurrently detrimentally affecting the ability of the compositions bond to a tooth surface or to bond a tooth surface to additional dental materials. In particular, it has now been found that certain oils do not interfere with free radical polymerization and/or acid-base reactions in the amounts used, and as a result, these oils can be utilized in conventional compositions to provide the aforementioned benefits.

The oils useful in the present invention are thus those oils which are capable of altering the sensory properties of conventional materials and/or providing the materials, when hardened in the mouth, with a more hydrophobic surface than the hardened surface of a material not comprising an essential oil, without detrimentally affecting the ability of the composition to form permanent bonds with the tooth surface or other dental materials, i.e., that do not interfere with free radical polymerization, and which are orally non-toxic. Generally speaking, these qualities are embodied by "essential" oils, i.e., oils which are derived from plant sources or animal sources. Examples of such oils include, but are not limited to, soybean oil, safflower oil, sesame oil, olive oil, sunflower oil, canola oil, walnut oil, peanut oil, orange oil, eucalyptus oil, cod liver oil, castor oil, combinations thereof, and the like. Such oils are readily commercially available from a variety of sources as will be readily appreciated by one of ordinary skill in the art. Furthermore, inasmuch as these oils are consumable food items in reasonable quantities, oral toxicity is generally not a concern.

As used herein the phrase "non-metallic composition" is meant to indicate a tooth colored material that is used in the mouth to repair, replace or otherwise complement the surface of a tooth, whether applied to enamel or dentin, and that once placed in the mouth and caused to harden, forms a substantially permanent feature. Such materials include, for example, sealants, adhesives, composites, restoratives, and the like. Although there are many different types of each of these materials, e.g., resin composites, compomers, glass-ionomers and resin-modified glass-ionomers, the type of material into which the oil is to be incorporated is not particularly restricted, and in fact, it is believed that the oil may be mixed into many if not all types of the aforementioned materials and provide the advantages disclosed herein.

Resins and resin composites are materials that harden by a polymerization reaction mechanism. Generally, the polymerization reaction is a free radical addition polymerization, activated either by chemicals, or more usually, by visible light. Resins and resin composites may optionally contain inert inorganic fillers (silica, barium glass, zirconia/silica glass are some examples) to modify properties. These types of materials adhere micromechanically to tooth enamel following acid etching and bond to dentin via application of an acid conditioner followed by a primer and/or adhesive, after which application a combination of micromechanical and interdiffusion bonding occurs. As is well known to those of ordinary skill in the art, many different types of resins and resin composites are commercially available, and typically vary in the type, concentration and properties of the filler. Representative examples of commercially available resin composites include, but are not limited to, Revolution (Kerr Corporation, Orange, Calif.); Silux (3M, St Paul, Minn.); HRV Herculite (Kerr Corporation, Orange Calif.); Restorative Z 100 (3M, St Paul, Minn.); and Alert (Pentron Inc, Wallingford, Conn.).

Glass-ionomers sometimes referred to as polyalkenoate cements, set and/or harden via an acid-base reaction, wherein an acidic polymer or copolymer aqueous solution reacts with an ion-leachable glass. For example, poly(acrylic acid) and related copolymers—referred to here as PAA—can react with a fluoroaluminosilicate glass (FAS) to give a set product consisting of a core of some unreacted FAS surrounded by the acid-base reaction products. Glass-ionomers, when set, contain an aqueous phase, and also fluoride ions from the chemical breakdown of the FAS. These materials are capable of chemical adhesion to a tooth substance, because of ionic attraction between PAA anions and the calcium of enamel and dentin. Glass-ionomers are well-known compositions to those of ordinary skill in the art and are readily commercially available. One representative example of a commercially available glass-ionomer includes, but is not limited to, Ketac-Cem Radiopaque (Espe America, Inc, Norristown Pa.).

Resin-modified glass-ionomers are often used in situations wherein properties intermediate between those of resins and glass-ionomers are desired. Resin-modified glass-ionomers set and harden via a combination of an acid-base reaction and a polymerization reaction, which may be activated chemically and/or by the application of visible light. These materials, like glass-ionomers, contain an aqueous phase when set, which ensures that fluoride ions are present that can then leach from the hardened material over time. Resin-modified glass-ionomers are well-known compositions to those of ordinary skill in the art and are readily commercially available. One representative example of a commercially available resin-modified glass-ionomers includes, but is not limited to, GC Fuji II LC Improved (GC America Inc, Alsip, Ill.)

Compomers are also advantageously used in situations wherein properties intermediate between those achievable with resins and glass-ionomers are desired. Compomers are polyacid-modified resin composites that set and/or harden via a polymerization mechanism. Compomers are well-known compositions to those of ordinary skill in the art and are readily commercially available. One illustrative example of a commercially available compomer includes, but is not limited to, Compoglass® (Ivoclar North America Inc, Amherst, N.Y.).

The non-metallic compositions of the present invention may readily and conveniently be prepared at a point of use by one of ordinary skill in the art by simply combining the desired essential oil with any desired conventional non-metallic composition. Such combining may take place immediately prior to the use of the composition, or alternatively, the oil may be combined with the conventional composition and then stored until the use thereof is desired. If the composition is to be stored for a period of time, the conditions of storage are not substantially impacted by the inclusion of the essential oil, and thus compositions in accordance with the present invention may be stored in the manner appropriate for the conventional composition.

The oil is desirably included in the non-metallic composition in an amount that is effective to alter the sensory properties of the composition and/or to render the surface of the composition, when hardened, more hydrophobic than the corresponding conventional composition. As a lower limit, at least enough of the oil should be included so that the oil is at least capable of reducing or eliminating any other unpleasant flavors of the composition and/or rendering the surface of the hardened composition at least marginally more hydrophobic than its conventional counterpart. As an upper limit, not so much oil should be included so that the effectiveness of the composition is substantially detrimentally affected. Bearing these considerations in mind, and generally speaking, the amount of oil that is thought to achieve the aforementioned objectives will likely range from about 0.1 weight percent (wt %) to about 10 wt %, preferably from about 1 wt % to about 5 wt %, more preferably from about 1.5 wt % to about 3 wt %, based upon the weight of the conventional composition without the oil.

Of course, the particular amount of oil that is to be included in the composition will be dependent upon the particular conventional composition and oil chosen. For exemplary purposes only, and in that embodiment of the invention wherein the conventional composition is Restorative Z100 (3M, St. Paul, Minn.) and the oil is soybean oil, the oil is desirably included in the conventional composition in an amount of from about 0.1% to about 10% to prepare one representative non-metallic composition in accordance with the present invention.

Although it is contemplated that any of the essential oils listed above, or any other essential oil that does not substantially interfere with the ability of the composition to harden or cure to form a substantially permanent feature within the mouth, will be capable in some amount of at least minimizing the unpleasant flavor of, or imparting a pleasant flavor and/or odor to, any conventional composition, in some instances it may be desirable to impart a stronger flavor, or a particular flavor that is not readily available in an oil form. For example, children generally prefer sweeter and/or stronger flavors than adults and thus may prefer flavors such as cherry, strawberry, blueberry, watermelon, lemon, lime, raspberry, apple, grape, cranberry, coconut, banana, tangerine, pineapple, bubble bum, almond, hazelnut and the like, rather than spearmint or orange flavors. In these instances, the essential oil to be incorporated into the composition of the present invention may further have incorporated therein an amount of a flavoring agent such as those previously mentioned, i.e., the essential oil may act as a carrier for other flavoring agents. Such flavoring agents are readily commercially available as either syrups, solutions or solids, and may be incorporated into the essential oil simply by mixing the desired flavoring agent with the essential oil. Experiments have shown that the inclusion of such a flavoring agent in the essential oil will not have a detrimental effect on the ability of the composition to substantially bond another dental material to, or itself to bond with a tooth surface.

The non-metallic compositions of the present invention may optionally comprise other ingredients that may be used to further enhance the sensory and/or mechanical properties of the non-metallic compositions. For example, it has additionally been found that certain other liquids, such as glycerol or propylene glycol, can be used as carriers for the flavoring agents mentioned hereinabove while not substantially adversely affecting the properties of the compositions into which they are incorporated. Thus, such liquids can be used, either alone or in conjunction with the essential oils, to incorporate additional flavoring agents in those embodiments of the invention where this is desired.

The non-metallic compositions of the present invention, comprising an essential oil, are advantageous over conventional compositions in that they have either a lesser unpleasant flavor and/or odor than their conventional counterparts, or may even have a pleasant flavor relative to conventional compositions. Furthermore, the present inventive compositions, when hardened in the mouth, have a more hydrophobic surface than analogous conventional compositions. Surprisingly, utilizing an essential oil to provide these advantageous properties to conventional compositions does not adversely affect the ability of the inventive compositions to bond to a tooth surface, or to bond a tooth surface with other dental materials. As a result, the composition of the present invention may advantageously be used to repair, seal or alter the position of teeth (as by the adherence of orthodontic fixtures to the tooth) and thus the present invention provides both a method of repairing or sealing hard dental tissue, i.e., the surface of a tooth, whether it be a dentin or enamel surface, as well as a method of adhering a dental or orthodontic fixture to hard dental tissue.

More specifically, the methods of the present invention involve applying a non-metallic composition comprising an essential oil to the tissue to be so treated. The composition may be applied to the tissue that is to be repaired, sealed or have a fixture adhered thereto by any conventional method known to those of ordinary skill in the art. In applications wherein no further treatment is desired, i.e., where no other dental fixtures are to be placed or adhered, such as is the case in certain treatments to repair or seal the teeth, the composition is simply caused to harden on said tissue. The inclusion of the essential oil in conventional compositions surprisingly does not substantially adversely affect the ability of, or the manner in which, the conventional composition hardens or cures, and thus, the present inventive composition may be caused to harden or cure by the same method used to cause the corresponding conventional composition to harden or cure. In applications wherein a dental or orthodontic fixture is to be adhered to the tissue, the composition is applied to the tissue to be so treated, followed by the fixture. The composition is then caused to harden, thereby substantially permanently adhering the fixture to the tissue.

Beneficially, the bond strength that may be achieved between a hard dental tissue and the compositions of the present invention, or that is achieved between the tissue and another dental fixture by virtue of the inventive compositions, is comparable to that that is achievable when a conventional composition is utilized to treat a tooth surface, as is shown in Examples 5–8, hereinbelow.

The present invention will be described below with reference to the following representative examples, wherein bond strength was determined as follows.

EXAMPLE 1

The following experiment was conducted to evaluate the impact of the inclusion of an oil on the ability of conventional resin-based compositions to set or harden. In particular, ten percent by weight of each of 10 oils (soybean, canola, sesame, olive, orange, eucalyptol, almond, safflower, walnut and cod liver oil) and 5% by weight of ethanol, propylene glycol and glycerol was added to each of three resin based materials: Restorative Z100 (3M, St Paul, Minn.). Coltene Brilliant Dentin (Coltene/Whaledent, Mahwah, N.J.), and System 1+ adhesive (Ormco, Glendora, Calif.) to prepare non-metallic compositions in accordance with the present invention.

The compositions, along with control samples of the conventional resin-based composites, were then irradiated with blue light of wavelength 470–480 nm and minimum intensity 450 mW/cm$^2$ for 40 seconds (Visilux 2 curing light, 3M, St Paul, Minn.). Each inventive composition quickly hardened to form a set mass, similar to the conventional resin-based composites. It was observed that the inclusion of the oils resulted in the inventive compositions having a smoother texture relative to the conventional resin-based composites, thus rendering the inventive compositions easier to handle.

EXAMPLE 2

The following experiment was conducted to evaluate the impact of the inclusion of an oil on the ability of conventional resin-modified glass ionomer compositions to set or harden. In particular, ten percent by weight of each of 10 oils (soybean, canola, sesame, olive, orange, eucalyptol, almond, safflower, walnut and cod liver oil) and 5% by weight of ethanol, propylene glycol and glycerol was mixed with each of two resin-modified glass-ionomers (Vitremer, 3M, St Paul, Minn. and Fuji II LC, GC America, Alsip, Ill.) to prepare non-metallic compositions in accordance with the present invention.

The compositions, along with control samples of the conventional resin-modified glass ionomers, were then irradiated with blue light of wavelength 470–480 nm and minimum intensity 450 mW/cm$^2$ for 40 seconds (Visilux 2 curing light, 3M, St Paul, Minn.). Each inventive composition quickly hardened to form a set mass, similar to the conventional resin-modified glass-ionomers. This example thus shows that the inclusion of the oil does not interfere adversely with either the free radical addition polymerization (similar to Example 1) or with the ionic acid-base reaction between the PAA and the FAS.

EXAMPLE 3

This experiment was conducted to further investigate the effect of the inclusion of an oil on the acid base reaction between PAA and FAS. In particular, the ten oils listed in Examples 1 and 2, ethanol. propylene glycol and glycerol were each mixed with PAA samples having a weight average molecular weight of from about 20,000 to about 1,000,000 in aqueous form. In all cases, the oil or other carrier dissolved in the PAA, thereby allowing the inference that PAA exists in ionic form in the mixtures containing water. This provides a number of desirable characteristics. First, the ionic nature of PAA allows the acid-base reaction to occur. Also, there is an ionic nature to the mechanism of adhesion.

EXAMPLE 4

The following experiment was conducted to evaluate the impact of the inclusion of an oil on the ability of conventional compomer compositions to set or harden. In particular, ten percent by weight of each of 10 oils (soybean, canola, sesame, olive, orange, eucalyptol, almond, safflower, walnut and cod liver oil) and 5% by weight of ethanol, propylene glycol and glycerol was mixed with F2000 compomer (3M, St Paul, Minn.) to prepare non-metallic compositions in accordance with the present invention. These samples were irradiated as in Example 1.

In all cases setting occurred in a manner indistinguishable from the unmodified material.

EXAMPLE 5

The following experiment was conducted to evaluate the impact of the inclusion of an oil on the diametral tensile strength of conventional resin composites. In particular, two percent by weight of each of 10 oils (soybean, canola, sesame, olive, orange, eucalyptol, almond, safflower, vegetable and walnut) and 5% by weight of soybean oil was mixed with Restorative Z100 (3M, St Paul, Minn.) to prepare non-metallic compositions in accordance with the present invention.

The compositions were then placed in molds to form into cylindrical specimens of height 3 mm and diameter 3 mm. The cylindrical specimens, along with control samples of Restorative Z100, were then irradiated with blue light of wavelength 470–480 nm and minimum intensity 450 mW/cm$^2$ for 40 seconds (Visilux 2 curing light, 3M, St Paul, Minn.). The specimens were compressed diametrally in an Instron testing machine (model 4204, Intron, Canton. Mass.) at a rate of crosshead movement of 1 mm/min. The force (F) to fracture the specimens was recorded, and diametral tensile strength (DTS) calculated from the formula:

$$DTS=2F/\pi dh,$$

where h is the height of specimen and d is the diameter of the specimen. In each case the reported data are the mean of six determinations. All specimens were stored in distilled water at 37° C. for 24 hours prior to testing.

The results of this experiment are shown below in Table 1.

TABLE 1

Diametral Tensile Strength of Inventive Compositions

| Composition | DTS (MPa) |
| --- | --- |
| Control | 51.4 |
| 2% soybean oil | 48.9 |
| 2% canola oil | 46.7 |
| 2% sesame oil | 53.7 |
| 2% olive oil | 46.6 |
| 2% orange oil | 42.2 |
| 2% eucalyptol oil | 46.8 |
| 2% almond oil | 53.1 |
| 2% safflower oil | 48.9 |
| 2% vegetable oil | 52.4 |
| 2% walnut oil | 52.7 |
| 5% soybean oil | 43.8 |

This experiment thus shows that the present inventive compositions have diametral tensile strength values substantially equivalent, and in some cases superior, to conventional resin compositions.

EXAMPLE 6

The following experiment was conducted to evaluate the impact of the inclusion of an oil on the diametral tensile strength of conventional composites. In particular, two percent by weight of each of soybean oil was mixed with Vitremer (3M, St Paul, Minn.) to prepare non-metallic compositions in accordance with the present invention.

The compositions were then placed in molds to form into cylindrical specimens of height 3 mm and diameter 3 mm. The cylindrical specimens, along with control samples of Vitremer, were then irradiated with blue light of wavelength 470–480 nm and minimum intensity 450 mW/cm$^2$ for 40 seconds (Visilux 2 curing light, 3M, St Paul, Minn.). The specimens were compressed diametrally in an Instron testing machine (model 4204, Intron, Canton. Mass.) at a rate of crosshead movement of 1 mm/min. The force (F) to fracture the specimens was recorded, and diametral tensile strength (DTS) calculated as described above.

The control had a DTS of 25.3 MPa, whereas the inventive composition had a DTS of 21.4 MPa. This examples thus shows that the non-metallic compositions of the present invention are capable of having diametral tensile strength values substantially equivalent to those of conventional compositions.

EXAMPLE 7

This example was conducted to evaluate the bond strengths attainable by the present inventive compositions. In particular, extracted human teeth were used and each tooth was sectioned to give a portion of the tooth with an intact enamel surface. Each tooth portion was embedded in an autopolymerizing acrylic resin cement in an aluminum ring, to leave the enamel surface exposed. The surfaces were then polished wet under 5 lb pressure on 600 grit carborundum paper for 30 seconds in an automatic polishing machine (Buehler Ecomet 3 with Automat 2 powerhead, Buehler Ltd, Lake Bluff, Ill.). Each specimen was etched with Scotchbond etchant (3M, St Paul, Minn.) for 20 seconds, washed with distilled water for 20 seconds, then dried thoroughly by air from a pressure line.

To each surface, the control glass-ionomer (Vitremer, 3M, St. Paul, Minn.) was applied, or alternatively, Vitremer with 5% by weight of soybean oil, both of which were cured by the application of visible light of wavelength approximately 470–480 nm and intensity 450 mW/square centimeter (Visilux 2 curing light, 3M, St Paul, Minn.). The cements were used to secure stainless steel orthodontic brackets (Ormco, Glendora, Calif.) to smooth enamel. Specimens were stored in water at 37° C. for 24 hours in distilled water prior to testing.

Testing was carried out using a shear bond testing rig and described and illustrated by Holtan et al (*Journal of Dentistry*. vol 22, pages 92–96, 1994 Apr). The testing machine was Instron model 4204 (Instron, Canton, Mass.), used at a rate of cross head movement of 1 mm/min. Data are the mean of five determinations. Specifically, the shear bond strength of the conventional Vitremer was 2.47 MPa while the shear bond strength of the Vitremer with the 5% soybean oil was 2.27 MPa. These two values are not statistically significantly different. The relatively low values are due to the nature of the tests conducted. The addition of stainless steel brackets causes greater leverage forces to be exerted on the bond. The relatively lower pressure of the bond was caused by gentle placement of the bracket rather than cylinder formation approaches which were used in the previous examples. Also, the surface was polished very smooth, so relatively little micromechanical adhesion occurred. This example thus shows that the non-metallic compositions of the present invention are capable of forming bonds with strengths substantially equivalent to those of conventional compositions.

EXAMPLE 8

This example was conducted to evaluate the bond strengths attainable by the present inventive compositions. In particular, tooth surfaces were prepared as described above in connection with Example 7 Cylinders of either Restorative Z100 (3M, St Paul, Minn.) or of Restorative Z100 with 2% by weight of soybean oil and the cylinders cured by the application of visible light of wavelength approximately 470–480 nm and intensity 450 mW/square centimeter (Visilux 2 curing light, 3M, St Paul, Minn.). Specimens were stored in water at 37° C. for 24 hours in distilled water prior to testing.

Testing was carried out as described above in connection with Example 7. Data are the mean of five determinations. Specifically, the shear bond strength of the conventional Restorative Z100 was 21.4 MPa while the shear bond strength of the Restorative Z100 with the 2% soybean oil was 17.5 MPa. These two values are not statistically significantly different. This example thus shows that the non-metallic compositions of the present invention are capable of forming bonds with strengths substantially equivalent to those of conventional resin compositions

EXAMPLE 9

This example was conducted to illustrate the impact of the inclusion of an oil on the hydrophobocity of conventional resin based compositions. In particular, an amount of a conventional resin composition (Restorative Z100, 3M, St Paul, Minn.) as well as an amount of an inventive composition (Restorative Z100+2% soybean oil) were allowed to harden and the hydrophobicity of the hardened surface measured by a Cahn Dynamic Contact Angle Analyzer Model DCA-322 with Win-DCA software (Cahn Instruments, Madison, Wis.). The conventional composition was found to have a contact angle with water of 74°, while the inventive compositions was found to have a contact angle with water of 84°. That is, the surface of the inventive composition was shown to be more water repellant, less easily wettable and thus more resistant to the deposition of bacterial plaque.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of adhering one or more dental or orthodontic fixtures to dental tissue comprising:
    (a) applying to said tissue a non-metallic composition comprising an essential oil mixed with the non-metallic composition, wherein the composition does not contain a quaternary ammonium compound;
    (b) placing the dental or orthodontic fixture in adhesive contact with the composition; and
    (c) causing the composition to harden on said tissue by one or more of polymerization and/or a reaction to form a glass ionomer to adhere the fixture to the dental tissue in a manner so as to render the fixture a substantially permanent feature on the tissue.

2. The method of claim 1, wherein the fixture is a dental fixture.

3. The method of claim 2 wherein the dental fixture is a veneer, a crown, an inlay, or a bridge.

4. The method of claim 1, wherein the fixture is an orthodontic fixture.

5. The method of claim 4, wherein the orthodontic fixture is a ceramic bracket or a metal bracket.

6. The method of claim 1, wherein the composition forms a bond between the tissue and the fixture, and wherein the bond has a bond strength of at least about 13 MPa.

7. The method of claim 6, wherein the bond has a bond strength of from about 15 MPa to about 40 MPa.

8. A method for adhering one or more dental or orthodontic fixtures to hard dental tissue comprising:
    (a) applying to said tissue a non-metallic composition comprising an essential oil mixed with the non-metallic composition, wherein the composition does not contain an antiseptic or antibacterial compound;
    (b) placing the dental or orthodontic fixture in adhesive contact with the composition; and
    (c) causing said composition to harden on said tissue by one or more of polymerization and/or a reaction to form a glass ionomer to adhere the fixture to the dental tissue in a manner so as to render the fixture a substantially permanent feature on the tissue.

9. The method of claim 8, wherein the fixture is a dental fixture.

10. The method of claim 9, wherein dental fixture is a veneer, a crown, an inlay, or a bridge.

11. The method of claim 8, wherein the fixture is an orthodontic fixture.

12. The method of claim 11, wherein the fixture is a ceramic bracket or a metal bracket.

13. A method for adhering one or more dental or orthodontic fixtures to hard dental tissue comprising:
   (a) applying to said tissue a non-metallic composition comprising an essential oil mixed with the non-metallic composition, wherein the essential oil is selected from the group consisting of soybean oil, safflower oil, sesame oil, olive oil, sunflower oil, canola oil, walnut oil, peanut oil, orange oil, cod liver oil, castor oil, and combinations thereof;
   (b) placing the dental or orthodontic fixture in adhesive contact with the composition; and
   (c) causing said composition to harden on said tissue by one or more of polymerization and/or a reaction to form a glass ionomer to adhere the fixture to the dental tissue in a manner so as to render the fixture a substantially permanent feature on the tissue.

14. The method of claim 13, wherein the fixture is a dental fixture.

15. The method of claim 14, wherein dental fixture is a veneer, a crown, an inlay, or a bridge.

16. The method of claim 13 wherein the fixture is an orthodontic fixture.

17. The method of claim 16 wherein the fixture is a ceramic bracket or a metal bracket.

18. The method of claim 13 wherein the composition hardens by free-radical polymerization.

19. A method for adhering one or more dental or orthodontic fixtures to hard dental tissue comprising:
   (a) applying to said tissue a non-metallic composition comprising an essential oil mixed with the non-metallic composition,
   (b) placing the dental or orthodontic fixture in adhesive contact with the composition; and
   (c) causing said composition to harden on said tissue by a reaction to form a glass ionomer.

20. The method of claim 19 wherein the essential oil is selected from the group consisting of soybean oil, safflower oil, sesame oil, olive oil, sunflower oil, canola oil, walnut oil, peanut oil, orange oil, eucalyptus oil, cod liver oil, castor oil, and combinations thereof.

21. The method of claim 19 wherein the essential oil is selected from the group consisting of soybean oil, safflower oil, sesame oil, olive oil, sunflower oil, canola oil, walnut oil, peanut oil, orange oil, cod liver oil, castor oil, and combinations thereof.

22. The method of claim 19 wherein the essential oil comprises soy oil.

23. A method for adhering one or more dental or orthodontic fixtures to hard dental tissue comprising:
   (a) applying to said tissue a non-metallic composition comprising a flavorant carried in an essential oil carrier mixed with the non-metallic composition,
   (b) placing the dental or orthodontic fixture in adhesive contact with the composition; and
   (c) causing said composition to harden on said tissue by one or more of polymerization and/or a reaction to form a glass ionomer.

24. The method of claim 23 wherein the essential oil is selected from the group consisting of soybean oil, safflower oil, sesame oil, olive oil, sunflower oil, canola oil, walnut oil, peanut oil, orange oil, eucalyptus oil, cod liver oil, castor oil, and combinations thereof.

25. The method of claim 23 wherein the essential oil is selected from the group consisting of soybean oil, safflower oil, sesame oil, olive oil, sunflower oil, canola oil, walnut oil, peanut oil, orange oil, cod live oil, castor oil, and combinations thereof.

26. The method of claim 23 wherein the essential oil comprises soy oil.

* * * * *